United States Patent
Kobayashi et al.

(12)

(10) Patent No.: US 6,339,159 B1
(45) Date of Patent: Jan. 15, 2002

(54) OPTICALLY ACTIVE α-AMINONITRILE AND PROCESS FOR PRODUCING α-AMINO ACID

(75) Inventors: Shu Kobayashi; Haruro Ishitani, both of Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/831,708

(22) PCT Filed: Mar. 13, 2000

(86) PCT No.: PCT/JP00/01508

§ 371 Date: Jul. 13, 2001

§ 102(e) Date: Jul. 13, 2001

(87) PCT Pub. No.: WO01/19787

PCT Pub. Date: Mar. 22, 2001

(30) Foreign Application Priority Data

Sep. 14, 1999 (JP) .......................................... 11-261210

(51) Int. Cl.[7] ..................... C07D 211/60; C07D 253/00; C07D 229/00
(52) U.S. Cl. ........................ 546/227; 568/332; 568/345; 568/346; 562/433; 562/452
(58) Field of Search ........................... 546/227; 558/332, 558/345, 346; 562/433, 452

(56) References Cited

U.S. PATENT DOCUMENTS 4,916,251 A * 4/1990 Morgan ....................... 558/332
4,962,223 A * 10/1990 Cannata et al. .............. 558/408

FOREIGN PATENT DOCUMENTS

| JP | 11-253813 | 9/1999 |
| WO | 91/17141 | 11/1991 |

OTHER PUBLICATIONS

H. Ishitani et al., J. Am. Chem. Soc., vol. 122, No. 5, pp. 762–766 (2000).
H. Ishitani et al., Angew. Chem. Int. Ed., vol. 37, No. 22, pp. 3186–3188 (1998).

* cited by examiner

Primary Examiner—Alan L. Rotman
Assistant Examiner—Raymond Covington
(74) Attorney, Agent, or Firm—Wenderoth, Lind & Ponack, LLP

(57) ABSTRACT

An aldehyde compound is reacted with an amino compound and hydrogen cyanate in the presence of a chiral zirconium catalyst obtained by mixing a zirconium alkoxide with an optically active binaphthol compound.

7 Claims, No Drawings

OPTICALLY ACTIVE α-AMINONITRILE AND PROCESS FOR PRODUCING α-AMINO ACID

TECHNICAL FIELD

The present invention relates to a method for producing optically active α-aminonitriles and α-amino acids. More specifically, the invention relates to a novel method, which enables the synthesis of optically active α-aminonitriles followed by the synthesis of optically active α-amino acids in high yield and high stereoselectivity.

BACKGROUND ART

Various α-amino acids and α-aminonitriles, as intermediates thereof, are useful substances in various fields such an pharmaceuticals, agricultural chemicals, toiletries and other such chemical products, an well an in the fold of functional polymers.

With respect to the synthesis of these useful substances, lately, there have been some reports on the method of catalytic asymmetric synthesis of α-aminonitriles.

However, since such formerly reported methods of asymmetric synthesis use isolated and purified imines, in most cases, problems such as the limit in their application to imines derived from unstable aliphatic aldehydes, and low asymmetric yield exist.

Therefore, in the present invention, the object is to provide a solution to the above-mentioned problems of the conventional asymmetric synthesis, and to provide a novel method which enables the synthesis of optically active α-aminonitriles, and further, the synthesis of optically active α-amino acids, in high asymmetric yield, without going through imines, even when using unstable aldehydes as starting materials.

DISCLOSURE OF INVENTION

The present invention firstly provides, as a means to solve the above-mentioned problems, a method for producing optically active α-aminonitriles, which comprises reacting an aldehyde compound, an amino compound and hydrogen cyanate in the presence of a chiral zirconium catalyst obtained by mixing a zirconium alkoxide with at least one optically active binaphthol compound.

Also, the present invention secondly provides a method for producing optically active α-aminonitriles, wherein the optically active binaphthol compound is at least one compound selected from 3,3'-dibromo-1,1'-bi-2-naphthol and 6,6'-dibromo-1,1'-bi-2-naphthol. The invention thirdly provides a method for producing optically active α-aminonitrile, wherein the reaction in conducted in the presence of an imidazole compound.

Further, the present invention fourthly provide the method for producing optically active α-aminonitriles according to any one of the first to third inventions, wherein an aldehyde compound represented by the formula

R¹CHO (wherein R¹ represents a hydrocarbon group which may include one or more substituents) in reacted with an amino compound represented by the formula

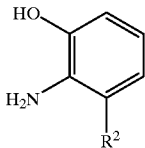

(wherein R² represents a hydrogen atom or a hydrocarbon group which may include a substituent) and hydrogen cyanate to produce an optically active α-aminonitrile represented by the formula

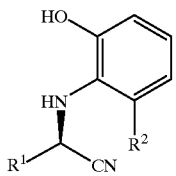

(wherein R¹ and R² are as described above).

Furthermore, the present invention fifthly provides a method for producing an optically active α-amino acid, which comprises converting the cyano group of the optically active α-aminonitrile produced by any one of the methods of the first to fourth inventions to a carboxyl group or its derivative.

Also, the invention provides, sixthly, a method for producing an optically active α-amino acid ester, which comprises converting the cyano group of the α-aminonitrile obtained by the method of the fourth invention to an ester group, followed by its oxidative decomposition to form an optically active α-amino acid ester represented by the formula

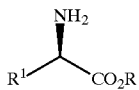

(wherein R and R¹ are hydrocarbon groups which may include one or more substituents).

Seventhly, the present invention provides a method for producing a pipecolic acid outer represented by the formula

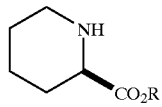

(wherein R is as described above) which comprises the deprotection and protection of the phenolic hydroxyl group of the α-aminonitrile of the following formula

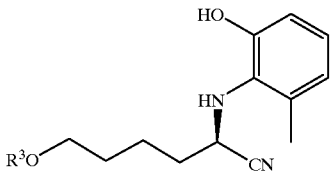

(wherein $R^3$ represents a protecting group), obtained by the process of the fourth invention to form the compound represented by the formula

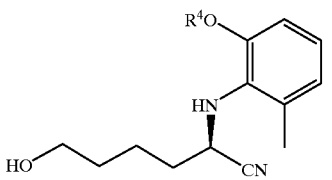

(wherein $R^4$ represents a protecting group), followed by cyclization and esterification to form the ester compound represented by the formula

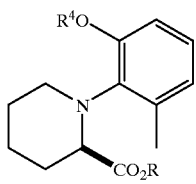

(wherein $R^4$ is an described above, and R represents a hydrocarbon group which my contain one or more substituent), which is then oxidatively decomposed.

The invention described above enables new development in the long-known Strecker synthesis. That is, although the Strecker synthesis is a method for producing synthetic amino acids wherein α-aminonitriles are synthesized by the main-component condensation of ammonia, aldehyde and hydrogen cyanate, development of this method as a method of asymmetric synthesis has been an unexplored task. Under the situation, the inventors of the prevent invention have so far proposed the asymmetric Strecker-type reaction using trialkyltin cyanide as the cyano source (Japanese Patent Provisional Publication No. 255,730/1999). In the present invention, the formation of α-aminonitriles by asymmetric synthesis using hydrogen cyanate as a cyano source is enabled.

In other words, the method for producing the optically active α-aminonitrile of the present invention enables the realization of the asymmetric synthesis of α-aminonitriles in high yield, directly from aldehyde compounds, amino compounds and hydrogen cyanate without going through an imine as in formerly known methods.

Further, the present invention also enables the production of optically active α-amino acid in high yield.

BEST MODE FOR CARRYING OUT THE INVENTION

The best mode for carrying out the invention described above in as described bellow.

Basically, in the invention,
(I) an aldehyde compound,
(II) an amino compound, and
(III) hydrogen cyanate (HCN),
are used as the starting materials, reacted in the liquid phase in the presence of
(IV) a chiral zirconium catalyst to asymmetrically synthesize α-aminonitrile.

The starting materials, the aldehyde compound (I) and the amino compound (II), maybe aldehydes and amines of various structures, such an aliphatic, alicyclic, aromatic, araliphatic or heterocyclic aldehydes and amines. The method of the present invention is applicable to unstable substances such as aliphatic aldehydes which were deemed to be unusable in formerly known asymmetric synthesis of α-aminonitriles, which were performed via imines.

In the aldehyde compound (I), an aldehyde group (—CHO) may be bound to primary, secondary or tertiary carbon atoms, $CH_2$—, CH— or C—. Further, the amino compound (II) may be a primary amine or a secondary amine with amino groups such as $NH_2$ and NH. It is preferable to use a primary amine (—$NH_2$) compound as the amino compound (II).

The chiral zirconium catalyst (IV) used in the present invention is obtained by mixing a zirconium alkoxide of the following formula $$Zr(OR)_4$$

(wherein R in a hydrocarbon group which may contain one or more substituents), with an optically active binaphthol compound. The hydrocarbon group constituting the alkoxy group (—OR) of the zirconium alkoxide may be aliphatic, alicyclic aromatic or other hydrocarbon groups, but is preferably an aliphatic hydrocarbon group such as an alkyl group. Appropriate examples of such alkyl group include lower alkyl groups such as a methyl group, an ethyl group, an n-propyl group ("Pr), an isopropyl group ($^i$Pr), an n-butyl group ("Bu), an isobutyl group ($^i$Bu), a tert-butyl group ($^t$Bu), an n-pentyl group ("Pent), an isopentyl group ($^i$Pent) and an n-hexyl group ("Hex).

The four alkoxide group (—OR) constituting the zirconium alkoxide ($Zr(OR)_4$) may all be the same or different.

The optically active binaphthol compound to be mixed with the zirconium alkoxide may contain appropriate substituents in the naphthalene ring, and more than one optically active binaphthol compounds may be used in the mixing. Examples of the substituent are a halogen atoms such as chlorine, bromine or fluorine, alkyl groups, alkoxy groups, halo-substituted alkyl groups and alkoxy-substituted alkyl groups. Binaphthol compounds having the same substituents in a symmetric position on the two naphthalene rings is more preferable. Specific examples thereof include optically active 3,3'-dibromo-1,1'-bi-2-naphthol and optically active 6,6'-dibromo-1,1'-bi-2-naphthol.

In the reaction, the zirconium alkoxide and the binaphthol compound may be added to the reaction system in a premixed state or may be mixed in the reaction system.

Also, in such asymmetric synthesis, which uses chiral zirconium catalyst (IV) of the present invention, a nitrogen-containing compound, preferably, a nitrogen-containing compound forming a tertiary amino group, such as an N-alkyl-substituted imidazole compound, may be present in the reaction system. The presence of such nitrogen-containing compound may improve the reactivity.

In the method of asymmetric synthesis of α-aminonitriles of the present invention, an appropriate reaction solvent may be used. Examples of such solvent include halogenated hydrocarbons, acetonitrile, DMF and DMSO.

The amount of the starting materials and the catalyst used in the asymmetric synthesis are not particularly limited; however, for the starting materials, the molar ratio, aldehyde compound (I)/amino compound (II)/HCN(III), may generally be controlled to 1/0.1 to 10/0.1 to 10. Further, for the chiral zirconium catalyst (IV), the amount of the zirconium alkoxide is preferably 1 to 20 mol %, the amount of the binaphthol 1 to 50 mol %, and the amount of the nitrogen-containing compound 40 mol % or less.

In the method for asymmetric synthesis of α-aminonitrile of the present invention, the reaction temperature is preferably −70° C. to 30° C. Further, the reaction pressure may be reduced bellow atmospheric pressure or in the rage of atmospheric pressure to 2 atm.

Considering the toxicity of hydrogen cyanate, the reaction is preferably conducted under low temperature, in the presence of a solvent that excels in absorption solubility of hydrogen cyanate, or pressurize by an inert gas such as argon or nitrogen. The starting material, hydrogen cyanate (HCN), may be supplied as a gas or may be generated in the liquid phase of the reaction system.

From the method of the present invention, for example, an optically active α-(N-aryl-substituted amino) nitrile compound is obtained in high yield by the reaction of an aldehyde compound ($R^1CHO$) with a 2-hydroxy-6-$R^2$-substituted-aniline and HCN, as stated above.

Such α-aminonitrile enables the selective formation of optically active α-amino acids, through the decomposition of the cyano group or the convertion to a carboxyl group or its derivative such as an ester group through esterification.

Some of the optically active α-amino acids are important because they possess bioactivity or biological activity. Further, selective synthesis of pipecolic acid may also he realized through the prevent invention, as stated earlier.

The invention in illustrated more specifically by referring to the following Examples.

EXAMPLES

Example 1

As an optically active α-aminonitrile, 1-(2-Hydroxy-6-methyl)amino-3-methylbutane-1-carbonitrile was synthesized according to the following reaction scheme:

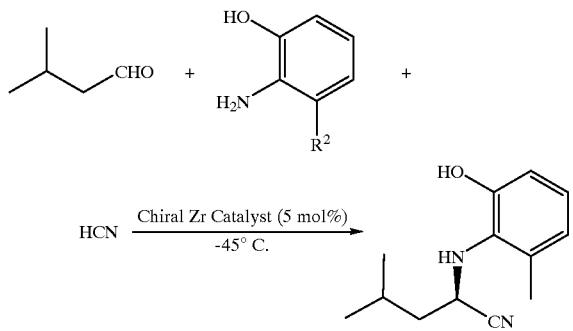

First, 2 equivalents of Zr(O$^t$Bu)$_4$, 2 equivalents of (R)-6,6'-dibromo-1,1'-bi-2-naphthol ((R)-6-Br-BINOL), 1 equivalent of (R)-3,3'-dibromo-1,1'-bi-2-naphthol((R)-3-Br-BINOL) and 3 equivalents of N-methylimidazole (NMI) were mixed in toluene to prepare a chiral zirconium catalyst. To this chiral zirconium catalyst (5 mol %, 0.04 M) were added isobutyl aldehyde, 2hydroxy-6-methylaniline and HCN in the presence of molecular sieve (4 A), at a temperature of −45° C., and stirred for 12 hours (Example 1-1).

The reaction was quenched by the addition of a saturated NaHCO$_3$ aqueous solution. The crude product was separated and purified by silica gel chromatography. The optical purity was determined through HPLC with a chiral column.

As a result, it was identified that an optically active 1-(2-hydroxy-6-methyl)amino-3-methylbutane-1-carbonitrile with an optical purity of 65 ee % was obtained in a 63% yield.

A reaction similar to that of Example 1-1 was conducted, wherein HCN was first added to the catalyst solution which was then added to a mixture of the aldehyde and the amine. As a result, the yield was 49%, and the optical purity was 79 ee % (Example 1-2). Then, this reaction was conducted by changing the solvent from toluene to dichloromethane. As a result, the yield became 63%, and the optical purity 85 ee % (Example 1-3). Thus, an improvement in the selectivity was observed.

Furthermore, the reaction was conducted in the foregoing manner with the catalyst concentration changed to 0.01 M, dichloromethane used as the solvent and the molecular sieve absent. As a result, the yield obtained was 99% and the optical purity was 94ee %. Thus, extremely high yield and selectivity were obtained (Example 1–4).

The above results are shown in Table 1.

TABLE 1

| Example 1- | Solvent | Molecular Sieves | Catalyst Concentration M | Yield % | Optical Purity ee % |
|---|---|---|---|---|---|
| 1[a] | Toluene | 4A | 0.04 | 63 | 65 |
| 2[b] | Toluene | 4A | 0.04 | 49 | 79 |
| 3[b] | Di-chloromethane | 4A | 0.04 | 63 | 85 |
| 4[b] | Di-chloromethane | none | 0.01 | 99 | 94 |

[a]Aldehyde amine and HCN added to catalyst
[b]HCN added to catalyst followed by addition of aldehyde and amine Since these compounds were unstable, the phenolic hydroxyl groups thereof were methoxylated with 20% methyl iodide-acetone (5 ml) and K$_2$CO$_3$ (200 mg) prior to their characterization.

The results of HPLC of the compounds with OH and the characterization of the methoxylated compounds are shown in the following table 2:

Examples 1-1 to 1-4 (Compound 2a)

Table 2
1-(2-Hydroxy-6-methylphenyl)amino-3-methylbutane-1-carbonitrile (Example 1, Compound 2a HPLC (Daicel Chiralpak AS, hexane/$^i$PrOH=9/1, flow rate=1.0 ml/min): $t_R$=8.3 min (major), $t_R$=10.2 min (minor).
1-(2-Methoxy-6-methylphenyl)amino-3-methylbutane-1-carbonitrile $^1$H NMR (CDCl$_3$) δ=1.00 (d, 3H, J=6.6 Hz), 1.03 (d, 3H, J=6.6 Hz), 1.80–1.83 (m, 2H), 1.99–2.07 (m, 1H), 2.30 (s, 3H), 3.71 (m, 1H), 3.85 (s, 3H), 4.20 (t, 1H, J=7.6 Hz), 6.76–6.79 (m, 2H), 6.95 (t, 1H, J=7.8 Hz); $^{13}$C NMR (CDCl$_3$) δ=17.8, 22.0, 22.5, 24.9, 43.2, 47.4, 55.8, 109.0, 120.6, 123.3. 123.5, 130.5, 132.8, 152.0, HRMS calcd for C$_{14}$H$_{20}$N$_2$O (M$^-$) 232.1576 found 232.1589.

With respect to the chiral zirconium catalyst, it is considered, from NMR analysis after the removal of the solvent, that during the reaction the catalyst is present in the structure of the following formula,

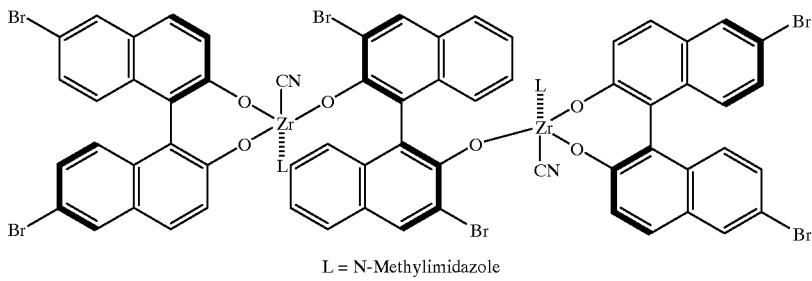

L = N-Methylimidazole wherein the cyano group (CN) does not act as a cyano source for the reaction.

Example 2

The reaction of the following scheme

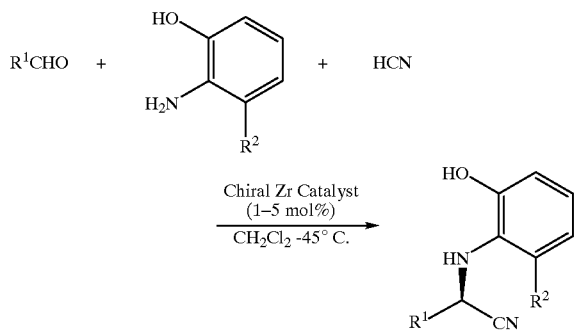

was conducted in the name manner as in Example 1, using various aldehyde compounds and amino compounds, with 1 to 5 mol % of the chiral zirconium catalyst, using dichloromethane as the solvent, at a reaction temperature of −45° C.

Various α-aminonitriles were obtained in high yield and high selectivity as shown in Table 3.

TABLE 3

| Example 2- | $R^1$ | $R^2$ | Catalyst Concentration mol % | Yield % | Optical Purity ee % |
|---|---|---|---|---|---|
| 1 | Ph | H | 5 | 80 | 86 |
| 2 | α-Nap | H | 5 | 83 | 85 |
| 3 | Ph(CH$_2$)$_2$ | CH$_3$ | 2.5 | 85 | 94 |
| 4 | C$_8$H$_{17}$ | CH$_3$ | 2.5 | 76 | 92 |
| 5 | C$_8$H$_{17}$ | CH$_3$ | 1 | 86 | 84 |
| 6 | C$_8$H$_{17}$ | CH$_3$ | 2.5 | 93 | 91[d] |
| 7 | C$_8$H$_{17}$ | CH$_3$ | 2.5 | 95 | 91[e] |
| 8 | $^i$Bu | CH$_3$ | 5 | 99 | 94 |
| 9 | $^i$Bu | CH$_3$ | 2.5 | 94 | 91 |
| 10 | c-C$_6$H$_{11}$ | CH$_3$ | 2.5 | 95 | 94 |
| 11 | $^t$Bu | CH$_3$ | 5 | quant | 86 |
| 12 | $^t$Bu | CH$_3$ | 2.5 | quant | 88[d] |

[d](O$^n$Pr)$_4$ used instead of Zr(OtBu)$_4$
[e](S)-3-Br-BNOL and (S)-6-Br-BINOL used.

Also, by using the chiral zirconium catalyst prepared by using Zr(O$^n$Pr)$_4$ (zirconium tetra "propoxide) instead of Zr(O$^t$Bu)$_4$ (zirconium tetra $^t$butoxide), high selectivity of 91 ee % and 88 ee % were obtained in a 93% yield and quantitative yield.

Further, by using (S)-3-Br-BINOL and (S)-6-Br-BINOL as the optically active binaphthol, excellent results with a yield of 95% and an optical purity of 91 ee % were obtained.

The results of HPLC and the characterization of the compounds shown in Table 3 are shown below. For unstable compounds, the characterization was conducted for the methoxylated compounds, as in Example 1.

Example 2-1

Table 4

2-(2-Hydroxyphenyl)amino-2-phenylacetonitrile (Example 2-1)

HPLC (Daicel Chiralcel OD, hexane/$^i$PrOH=9/1, flow rate=1.0 ml/min): $t_R$=40.0 min (major), $t_R$=49.7 min (minor). $^1$H NMR (CDCl$_3$) δ=4.43 (br, 1H), 5.40 (d, 1H, J=7.2 Hz), 6.72–6.93 (m, 4H), 7.43–7.61 (m, 6H); $^{13}$C NMR (CDCl$_3$)) ?=50.6, 114.2, 114.9, 118.4, 120.7, 121.5, 127.2, 129.3, 129.5, 133.3, 134.0, 144.5.

2-(2-Methoxyphenyl)amino-2-phenylacetonitrile $^1$H NMR (CDCl$_3$) δ=3.81 (s, 3H), 4.67 (d, 1H, J=8.3 Hz), 5.43 (d, 1H, J=8.3 Hz), 6.90–6.95 (m, 4H), 7.42–7.47 (m, 3H), 7.59–7.62 (m, 2H); $^{13}$C NMR (CDCl$_3$) δ=49.8, 55.4, 110.0, 111.6, 118.2, 119.6, 121.2, 127.2, 129.2, 129.4, 134.1, 134.5, 147.4, HRMS calcd for C$_{15}$H$_{14}$N$_2$O (M$^+$) 238.1107 found 238.1093.

Example 2-2

Table 5

2-(2-Hydroxyphenyl)amino-2-a-naphthylacetonitrile (Example 2-2)

HPLC (Daicel Chiralpak AD, hexanes/$^i$PrOH=9/1, flow rate=1.0 ml/min): $t_R$=28.5 min (minor), $t_R$=33.7 min (major). $^1$H NMR (CDCl$_3$) δ=4.43 (d, 1H, J=7.8 Hz), 5.73 (br, 1H), 5.95 (d, 1H, J=7.8 Hz), 6.67 (d, 1H, J=6.8 Hz), 6.73 (t, 1H, J=6.8 Hz), 6.92 (t, 1H, J=6.8 Hz), 6.98 (d, 1H, J=6.8 Hz), 7.41–7.49 (m, 3H), 7.82–7.92 (m, 4H); $^{13}$C NMR (CDCl$_3$) δ=48.5, 113.3, 114.9, 118.5, 120.4, 121.5, 122.7, 125.2, 126.2, 126.4, 127.3, 128.3, 129.0, 130.1, 130.5, 133.5, 133.9, 144.2.

Example 2-3

(Compound 2b)

Table 6

1-(2-Hydroxy-6-methylphenyl)amino-3-phenyl-propane-1-carbonitrile (Example 2-3, Compound 2b)

HPLC (Daicel Chiralpak AS, hexane/$^i$PrOH=19/1, flow rate=1.0 ml/min): $t_R$=30.7 min (major), $t_R$=34.2 min (minor). $^1$H NMR (CDCl$_3$) δ=2.18 (s, 3H), 2.19–2.27(m, 2H), 2.80–3.01 (m, 2H), 3.79 (br, 1H), 4.14 (t, 1H, J=6.7 Hz), 6.64–6.83 (m, 3H), 7.19–7.34 (m, 5H); $^{13}$C NMR (CDCl$_3$) δ=17.6, 32.9, 35.5, 48.3, 113.4, 120.3, 122.1, 123.7, 126.2, 128.2, 128.4, 130.9, 130.1, 139.7, 131.3, 139.7, 149.5, HRMS calcd for C$_{17}$H$_{18}$N$_2$O (M$^-$) 266.1420 found 266.1419.

Examples 2-4 to 2-7

Table 7

1-(2-Hydroxy-6-methylphenyl)aminonane-1-carbonitrile (Examples 2-4 to 2-7)

HPLC (Daicel Chiralpak AS, hexane/$^i$PrOH=19/1, flow rate=1.0 ml/min): $t_R$=10.4 min (major), $t_R$=13.0 min (minor). $^1$H NMR (CDCl$_3$) δ=0.89 (t, 3H, J=6.7 Hz), 1.20–1.70 (m, 12H), 1.92 (dt, 2H, J=7.3, 7.7 Hz), 2.33 (s, 3H), 4.00 (t, 1H, J=7.3 Hz), 6.70–6.93 (m, 3H); $^{13}$C NMR (CDCl$_3$) δ=14.0, 17.7, 22.6, 25.6, 29.0, 29.1, 29.3, 31.7, 34.2, 49.7, 113.4, 120.4, 123.0, 125.2, 130.6, 134.5, 150.1, HRMS calcd for C$_{17}$H$_{26}$N$_2$O (M$^+$) 274.2047, found 274.2045.

Example 2-10

Table 8

2-Cyclohexyl-2-(2-hydroxy-6-methylphenyl)aminoacetonitrile (Example 2-10)

HPLC (Daicel Chiralpak AS, hexane/$^i$PrOH=9/1, flow rate=1.0 ml/min): $t_R$=10.0 min (major), $t_R$=13.1 min (minor). $^1$H NMR (CDCl$_3$) ?=1.19–1.45 (m, 5H), 1.67–2.08 (m, 6H), 2.33 (s, 3H), 3.84 (d, 1H, J=6.1 Hz), 6.70–6.92 (m, 3H); $^{13}$C NMR (CDCl$_3$) ?=17.7, 25.6, 25.7, 25.9, 28.6, 29.5, 41.4, 55.3, 113.5, 119.6, 123.0, 125.1. 130.9, 132.3, 149.9. HRMS calcd for C$_{15}$H$_{20}$N$_2$O (M$^+$) 244.1577, found 244.1577.

Example 2-11 and 2-12

Table 9

2,2-Dimethyl-1-(2-hydroxy-6-methylphenyl)aminopropane-1-carbonitrile (Example 2-11 to 2-12)

HPLC (Daicel Chiralpak AD, hexane/$^i$PrOH=9/1, flow rate=1.0 ml/min): $t_R$=8.2 min (major), $t_R$=16.2 min (minor). $^1$H NMR (CDCl$_3$) δ=1.21 (s, 9H), 2.31 (s, 3H), 3.53 (br, 1H), 3.77 (br, 1H), 6.65–6.89 (m, 3H); $^{13}$C NMR (CDCl$_3$) δ=17.6, 25.9. 34.8, 59.6, 113.5, 119.5, 122.0, 124.6, 130.9, 131.9, 149.5. HRMS calcd for C$_{13}$H$_{12}$N$_2$O (M$^-$) 218.1420, found 218.1419.

Example 3

An α-amino acid ester compound was synthesized according to the following scheme:

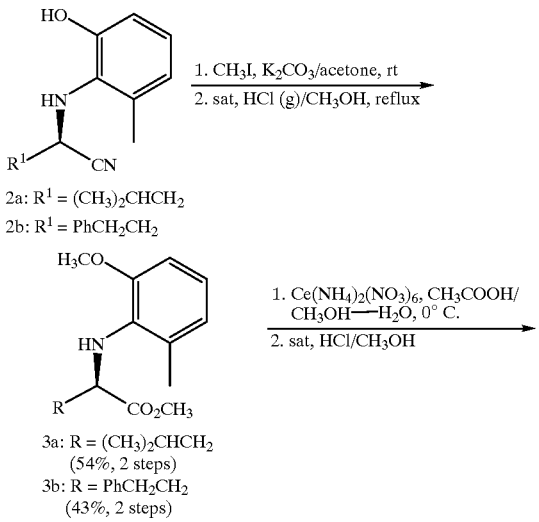

2a: R$^1$ = (CH$_3$)$_2$CHCH$_2$
2b: R$^1$ = PhCH$_2$CH$_2$

3a: R = (CH$_3$)$_2$CHCH$_2$ (54%, 2 steps)
3b: R = PhCH$_2$CH$_2$ (43%, 2 steps)

4a: R = (CH$_3$)$_2$CHCH$_2$ (>99%ee) (70%, 2 steps)
4b: R = PhCH$_2$CH$_2$ (>99%ee) (56%, 2 steps)

N-(2-hydroxy-6-methylphenyl)aminonitrile (compounds 2a, 2b), prepared as described in Example 2, was treated with CH$_3$I and K$_2$CO$_3$/acetone at room temperature to methoxylate the phenolic OH group, which was then refluxed with anhydrous HCl/methanol for 6 hours to convert the cyano group into methyl ester group. Consequently, an optically active N-substituted-α-aminocarboxylic acid methyl ester (compounds 3a, 3b) was obtained.

Methyl-2-(2-methoxy-6-methyl)phenylamino-4-methyl pentanoate (Compound 3a)

HPLC (Daicel Chiralpak AS, hexane/$^i$PrOH=1000/1, flow rate=1.0 ml/min): $t_R$=8.1 min (minor), $t_R$=11.0 min (major). $^1$H NMR (CDCl$_3$) δ=0.95 (d, 6H, J=6.4 Hz), 1.58–1.63 (m, 2H), 1.75–1.86 (m, 1H), 2.30 (s, 3H), 3.62 (s, 3H), 3.93 (bs, 1H), 4.24 (t, 1H, J=7.2 Hz) 6.68–6.82 (m, 3H); $^{13}$C NMR (CDCl$_3$) δ=18.2, 22.4, 22.6, 24.8, 43.4, 51.5, 55.6, 57.7, 109.1, 121.0, 123.4, 128.3, 134.8, 150.8, 175.7. HRMS calcd for C$_{15}$H$_{23}$NO$_3$ (M$^+$) 265.1679, found 265.1688.

Methyl-2-(2-methoxy-6-methyl)phenylamino-4-phenyl butanoate (Compound 3b)

HPLC (Daicel Chiralcel OJ, hexane/$^i$PrOH=19/1, flow rate=1.0 ml/min): $t_R$=8.1 min (minor), $t_R$=11.0 min (major). $^1$H NMR (CDCl$_3$) δ=0.95 (d, 6H, J=6.4 Hz); 1.58–1.63 (m, 2H), 1.75–1.86 (m, 1H), 2.30 (s, 3H), 3.62 (s, 3H), 3.93 (bs, 1H), 4.24 (t, 1H, J=7.2 Hz), 6,68–6.82 (m, 3H); $^{13}$C NMR (CDCl$_3$) δ=18.2, 22. HRMS calcd for C$_{19}$H$_{22}$NO$_2$(M$^+$) 313.1679, found 313.1678.

Compound 3a was oxidatively decomposed using cerium ammonium nitrate (CAN) to obtain leucine methyl ester (compound 4a) as the corresponding N-free-amino acid ester.

A more stable hydrochloride of compound 4a was easily obtained by treatment with HCl/methanol at a temperature of 0° C. The yield from compound 2a was 70%.

The optical purity of compound 4a was as high as 99 ee % or more.

The characterization of compound 4a is shown in table 10.

Compound 3a

Table 10

Leucine methyl ester (N-free amino ester) (Compound 4a)

$^1$H NMR δ=0.86–0.95 (m, 6H), 1.40–1.62 (m, 2H), 1.73–1.82 (m, 1H), 2.27 (bs, 2H), 3.52 (s, 3H); $^{13}$C NMR δ=21.8, 22.9, 24.7, 43.8, 51.9, 52.7, 176.8. HRMS calcd for C$_7$H$_{15}$NO$_2$ (M$^+$) 145.1104, found 145.1103.

Further, the results of HPLC after benzoylation are as follows.

Leucine methyl ester (after benzoylation)

HPLC (Daicel Chiralpak AS, hexane/$^i$PrOH=19/1, flow rate 1.0 ml/min); $t_R$=19.1 (minor), $t_R$=26.7 (major).

In the same manner, β-phenylalanine methyl ester of compound 4b was obtained from compound 3b.

The identification proportion and HPLC results are as follows:

β-Phenylalanine methyl ester (N-free amino ester) (Compound 4b)

$^1$H NMR δ=1.75 (br, 2H), 1.83–1.90 (m, 1H), 2.04–2.11 (m, 1H), 2.68 –2.78 (m, 2H), 3.47 (br, 1H), 3.71 (s, 3H), 7.18–7.30 (m, 5); $^{13}$C NMR δ=31.9, 36.4, 51.9, 53.9, 126.0, 128.39, 128.42, 141.2, 176.4. HRMS calcd for $C_{11}H_{15}NO_2$ (M$^-$) 193.1104, found 193.1102.

β-Phenylalanine methyl ester (after Benzoylation)

HPLC (Daicel Chiralcel OD, hexane/$^i$PrOH=9/1, flow rate 1.0 ml/min); $t_R$=24.4 (major), $t_R$=29.1 (minor).

Example 4

A D-pipecolic acid methyl ester was synthesized according to the following scheme:

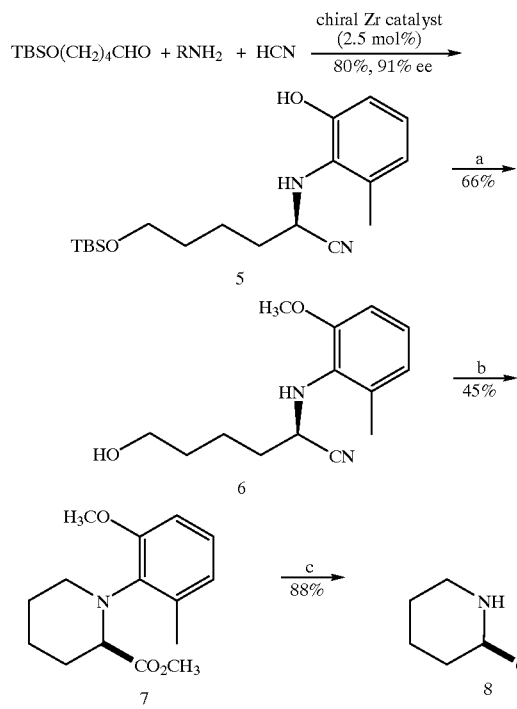

a: 1. CH$_3$I, K$_2$CO$_3$/acetone rt; 2. Bu$_4$NF/THF,
b: 1. CBr$_4$, PPh$_3$/CH$_2$Cl$_2$; 2. sat, HCl/CH$_3$OH, reflux,
c: 1. Ce(NH$_4$)$_2$(NO$_3$)$_6$, CH$_3$COOH/CH$_3$OH——H$_2$O, 0° C.

The results of HPLC and the identification properties of the compounds in the respective reaction steps are as follows.

Compound 5

5-tert-Butyldimethylsiloxy-1-(2-hydroxy-6-methylphenyl)aminopentane-1-carbonitrile (Compound 5)

HPLC (Daicel Chiralpak AS, hexane/$^i$PrOH 24/1, flow rate=0.5 ml/min): $t_R$=13.5 min (major), $t_R$=15.3 min (minor). $^1$H NMR (CDCl$_3$) δ=0.00 (s, 6H), 0.84 (s, 9H), 1.50–1.70 (m, 4H), 1.83–1.87 (m, 2H), 2.23 (s, 3H), 3.59 ( t, 2H, J=5.6 Hz), 3.99 (t, 1H, J=7.0 Hz), 6.59–7.28 (m, 3H); $^{13}$C NMR (CDCl$_3$) δ=−5.4, 17.7, 18.3, 22.0, 25.9, 31.9, 33.8, 49.4, 62.6, 113.4, 120.3, 122.8, 124.7, 130.8, 132.0, 149.8. HRMS calcd for $C_{20}H_{34}N_2O_2{}^{20}Si$ (M$^-$) 362.2391, found 362.2390.

Compound 6

5-Hydroxy-1-(2-methoxy-6-hydroxyphenyl)aminopentane carbonitrile (Compound 6)

$^1$H NMR (CDCl$_3$) δ=1.55–1.72 (m, 4H), 1.88–1.98 (m, 2H), 2.27 (s, 3H), 3.62 (t, 2H, J=5.9 Hz), 3.82 (s, 3H), 4.12 (t, 1H, J=6.9 Hz), 6.74–7.35 (m, 3H); $^{13}$C NMR (CDCl$_3$) δ=17.6, 21.8, 31.7, 33.7, 48.9, 55.7, 61.8, 108.9, 120.2, 123.2, 123.5, 130.5, 132.6, 152.0.

Compound 7

N-(2-Methoxy-6-methylphenyl)-pipecolic acid methyl ester (Compound 7)

$^1$H NMR (CDCl$_3$) δ=1.52–1.60 (m, 2H), 1.68–1.82 (m, 4H), 2.29 (s, 3H), 3.51 (t, 2H, J=6.6 Hz), 3.66 (s, 3H), 3.81 (s, 3H), 4.19 (t, 1H, J=7.5 Hz), 6.69–6.82 (m, 3H); $^{13}$C NMR (CDCl$_3$) δ=18.2, 22.8, 32.2, 33.0, 44.6, 51.7, 55.6, 58.8, 109.0, 121.1, 123.4, 128.4, 134.5, 150.8, 175.0, HRMS calcd for $C_{15}H_{21}N_2O_3$ (M$^-$) 263.1522, found 263.1521.

Compound 8

Pipecolic acid methyl ester (Compound 8)

$^1$H NMR (CDCl$_3$) δ=1.55–1.76 (m, 2H), 1.78–1.82 (m, 4H), 2.97 (br, 1H), 3.45–3.52 (m, 1H), 3.54 (t, 2H, J=6.7 Hz), 3.74 (s, 3H); $^{13}$C NMR (CDCl$_3$) δ=23.0, 29.7, 32.2, 44.6, 52.1, 52.9, 169.7.

INDUSTRIAL APPLICABILITY

As has ben described in detail above, according to the present invention, the asymmetric synthesis of α-aminonitriles and α-amino acids with high yield and high stereoselectivity is enabled, without going through imines, even when using unstable aldehyde as the starting material, as in the conventional methods.

What is claimed is:

1. A method for producing optically active α-aminonitrile, which comprises reacting an aldehyde compound, an amino compound and hydrogen cyanate in the presence of a chiral zirconium catalyst obtained by mixing a zirconium alkoxide with at least one optically active binaphthol compound.

2. The method according to claim 1, wherein the optically active binaphthol compound in at least one compound selected from 3,3'-dibromo-1,1'-bi-2-naphthol and 6,6'-dibromo-1,1'-bi-2-naphthol.

3. The method according to claim 1, wherein the reaction is conducted in the presence of an imidazole compound.

4. The method according to claim 1, wherein an aldehyde compound represented by the formula

R$^1$CHO (wherein R$^1$ represents a hydrocarbon group which may contain one or more substituent) is reacted with an amino compound represented by the formula

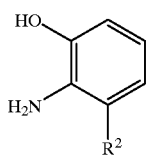

(wherein R$^2$ represents a hydrogen atom or a hydrocarbon group which may contain one or more substituents) and hydrogen cyanate to produce an optically active α-aminonitrile represented by the formula

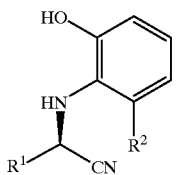

(wherein $R^1$ and $R^2$ are as described above).

5. A method for producing optically active α-amino acid, which comprises converting the cyano group of the optically active α-aminonitrile produced by the method of claim 1 to a carboxyl group or its derivative.

6. A method for producing an optically active α-amino acid ester, which comprises converting the cyano group of the α-aminonitrile obtained by the method of claim 4 to an eater group, followed by its oxidative decomposition to form an optically active α-amino acid ester represented by the formula

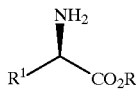

(wherein R and $R^1$ represent hydrocarbon groups which may contain one or more substituents).

7. A method for producing a pipecolic acid ester represented by the formula

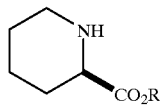

(wherein R is as described above), which comprises the deprotection and protection of the phenolic hydroxyl group of the α-aminonitrile

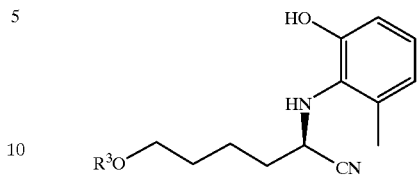

(wherein $R^3$ represents a protecting group), obtained by the method of claim 4, to form a compound represented by the formula

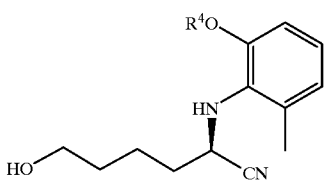

(wherein $R^4$ represents a protecting group), followed by its cyclization and esterification to form an ester compound represented by the formula

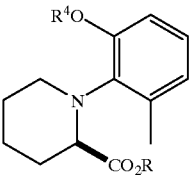

(wherein $R^4$ is as defined above and R represents a hydrocarbon group which may contain one or more substituent) followed by its oxidative decomposition.

* * * * *